US007967777B2

(12) United States Patent  
Edwards et al.

(10) Patent No.: US 7,967,777 B2
(45) Date of Patent: Jun. 28, 2011

(54) EYE TREATMENT SYSTEM WITH MULTIPLE PUMPS

(75) Inventors: Craig Edwards, Mission Viejo, CA (US); John I. Muri, Aliso Viejo, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 694 days.

(21) Appl. No.: 11/558,439

(22) Filed: Nov. 9, 2006

(65) Prior Publication Data

US 2008/0114372 A1   May 15, 2008

(51) Int. Cl.
*A61M 1/00* (2006.01)
(52) U.S. Cl. ............... 604/30; 604/34; 417/3; 606/107
(58) Field of Classification Search ............... 606/107; 604/30, 34, 35, 27; 417/477.2, 360
See application file for complete search history.

(56) References Cited

U.S. PATENT DOCUMENTS

| | | | |
|---|---|---|---|
| 4,276,023 A * | 6/1981 | Phillips et al. | 433/85 |
| 4,713,051 A * | 12/1987 | Steppe et al. | 604/30 |
| 4,904,168 A * | 2/1990 | Cavoto et al. | 417/477.2 |
| 4,920,336 A | 4/1990 | Meijer | |
| 5,041,096 A | 8/1991 | Beuchat et al. | |
| 5,125,891 A | 6/1992 | Hossain et al. | |
| 5,195,960 A | 3/1993 | Hossain et al. | |
| 5,230,614 A | 7/1993 | Zanger et al. | |
| 5,267,956 A * | 12/1993 | Beuchat | 604/30 |
| 5,364,342 A * | 11/1994 | Beuchat et al. | 604/30 |
| 5,454,783 A | 10/1995 | Grieshaber et al. | |
| 5,676,530 A | 10/1997 | Nazarifar | |
| 5,747,824 A | 5/1998 | Jung et al. | |
| 6,962,488 B2 | 11/2005 | Davis et al. | |
| 7,070,578 B2 | 7/2006 | Leukanech et al. | |
| 2003/0108429 A1 | 6/2003 | Angelini et al. | |
| 2005/0069419 A1 | 3/2005 | Cull et al. | |

FOREIGN PATENT DOCUMENTS

| | | |
|---|---|---|
| EP | 1829568 A1 | 9/2007 |
| WO | 02/28449 | 4/2002 |
| WO | 2005/084728 | 9/2005 |
| WO | WO 93/17729 | 11/2006 |
| WO | 2007001502 | 1/2007 |

\* cited by examiner

*Primary Examiner* — Kevin C. Sirmons
*Assistant Examiner* — Bradley G Thomas, Jr.

(57) ABSTRACT

An eye treatment system is configured for performing an ocular surgical procedure and includes an eye treatment probe, a treatment console including a controller, and an eye treatment cassette for coupling the eye treatment probe with the treatment console. The eye treatment probe is configured to provide at least irrigation fluid to, and aspiration of fluid from, a subject eye. The cassette comprises a cassette body, first and second arcuate ramps, and a holding tank. The cassette has an engagement axis along which elements of the cassette are configured to generally engage with mating elements of the treatment console. The cassette's first arcuate ramp is proximal a first fluidics channel configured to form a first volumetric pump upon engagement with the treatment console. Also the cassette's second arcuate ramp is proximal a second fluidics channel configured to form a second volumetric pump upon engagement with the treatment console. The cassette also includes a holding tank fluidly that is coupled to the volumetric pumps.

21 Claims, 8 Drawing Sheets

EYE TREATMENT SYSTEM WITH MULTIPLE PUMPS

BACKGROUND OF THE INVENTION

1. Field of the Invention

This invention relates generally to an eye treatment system, and more specifically to an eye treatment system utilizing multiple pumps.

2. Description of the Related Art

Volumetric and vacuum pumps are used for removing fluid and other material from a surgical site. For example, in ophthalmic surgical systems, a peristaltic pump may be used to precisely regulate the flow of fluid to and from the eye during a cataract, vitrectomy, or other surgical procedure. Alternatively, vacuum pumps, such as Venturi pumps or rotary vane pumps, may be preferred by some surgeon or offer advantages for certain types of procedures compared to volumetric pumps. In some cases, it may be desirable to offer both types of pumps in a single system. Examples of such configurations are discussed in U.S. Pat. No. 5,195,960, U.S. Patent Application No. 2003/0108429, and PCT Patent Application Publication WO 93/17729, all of which are herein incorporated by reference.

Surgical systems utilizing vacuum pumps are generally based on the flow of a gas or other fluid. Consequently, the vacuum source must generally be isolated from fluids being removed from the surgical site. A holding tank may be used to provide this function and to provide a location where fluid and other material removed from the surgical site can be stored. To provide isolation, the holding tank may be configured with a first port at or near the top of the tank that is coupled to the vacuum source and a second port at or near the bottom of the tank that is connected to an aspiration line from the surgical site.

In some instances, it is desirable to incorporate at least portions of the pumping system into a disposable or reusable cassette. In the case of ophthalmic surgical systems, the cassette interfaces with a surgical console and couples the console to a handpiece with a probe that is inserted into the eye. The cassette generally contains tubing or fluid channels for coupling the handpiece to irrigation and aspiration sources, as well as for coupling to a volumetric pump head located inside the surgical console. In addition, the cassette may contain a holding tank that is coupled to a vacuum source that is also located inside the surgical console.

In order to provide a cassette having relatively small, inexpensive form and to maintain tight control of the vacuum pressure provided to the handpiece, the holding tank of the cassette is also preferably small. The small size of the holding tank generally necessitates periodic draining of the holding tank into a collection bag that may be directly attached to the body of the cassette.

Consequently, there is a need to provide cassette designs that allow for several pumps to be coupled together in a package that is relatively small and that is able to be easily and quickly installed prior to a surgical procedure.

BRIEF DESCRIPTION OF THE DRAWINGS

Embodiments of the present invention may be better understood from the following detailed description when read in conjunction with the accompanying drawings. Such embodiments, which are for illustrative purposes only, depict the novel and non-obvious aspects of the invention. The drawings include the following listed figures.

DETAILED DESCRIPTION OF THE DRAWINGS

The present invention is generally directed to systems and related methods for providing both volumetric and vacuum pumps for removing fluid and other material from a location, particularly a surgical location such as the eye of a subject. Preferred embodiments of the invention include a fluidics cassette package that is detachably coupled to a console and contains hardware and control functions. The cassette may be configured with a holding tank to couple one or more vacuum pumps located in and/or controlled by the console. The system and/or cassette further comprise a volumetric pump configured to control the amount of fluid in the holding tank. Fluid and material removed from the holding tank may be stored in a waste bag, for example, attached to the cassette.

Embodiments of the present invention may find particular use in a surgical environment, for example, an ophthalmic surgical system for which fluidic components are generally discarded after use or sterilized in preparation for use in a subsequent procedure. In such embodiments, the cassette is generally configured to couple an eye treatment probe or handpiece with the console.

Figure 1:
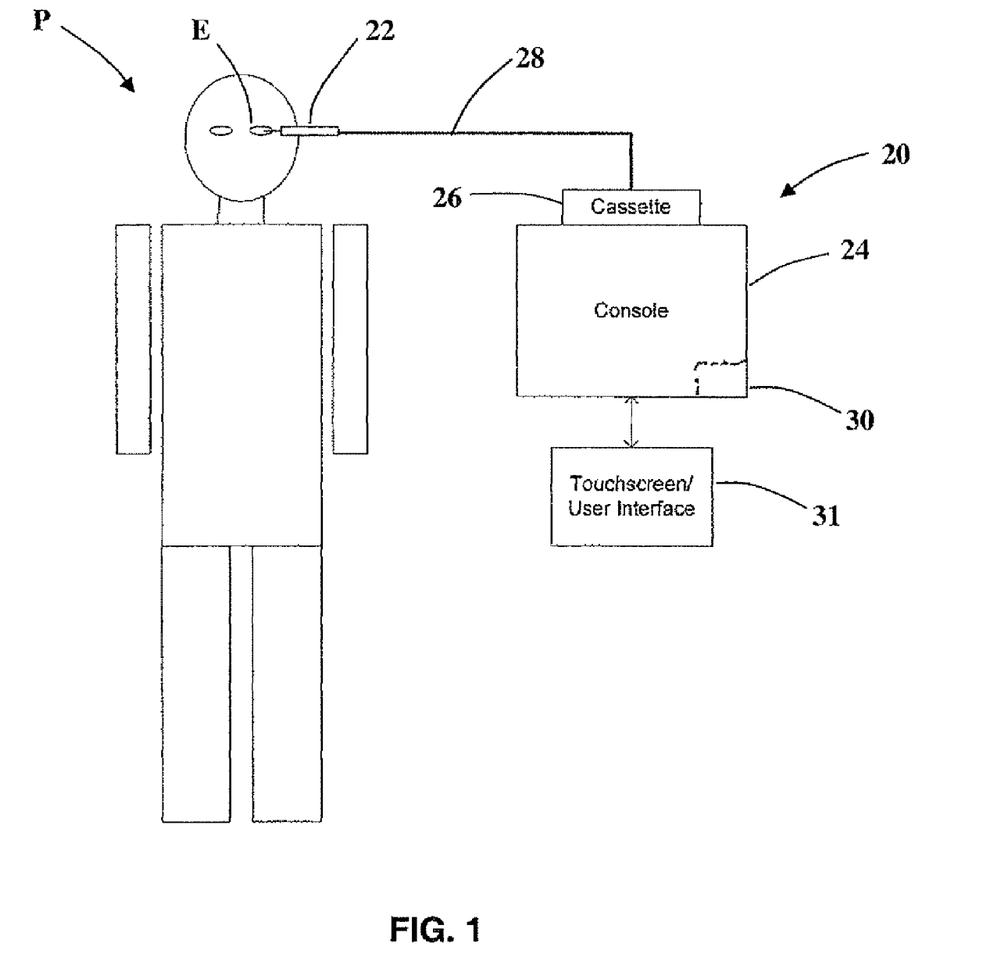
FIG. 1 is system diagram of a surgical system for use on the eye of a subject according to embodiments of the invention.

Referring to FIG. 1, in an exemplary embodiment, a surgical system 20 generally comprises an eye treatment probe or handpiece 22 that is coupled to a console 24 by a cassette 26 configured to supply irrigation and aspiration functions to the handpiece 22 via flexible conduits 28. Handpiece 22 may include a handle or gripping portion for manually manipulating and supporting an insertable probe tip. The probe tip includes a distal end that is insertable into an eye E of a patient P, with one or more lumens in the probe tip allowing irrigation fluid to flow into the eye E. Aspiration fluid may also be withdrawn through a lumen of the probe tip, with the console 24 and/or the cassette 26 generally including a vacuum aspiration source and at least one positive displacement or volumetric aspiration pump.

When the distal end of the probe tip of handpiece 22 is inserted into the eye E, an electrical conductor and/or pneumatic line (not shown) may also be provided between the console 24 and the handpiece 22. For example, to enable phacoemulsification of the natural lens in the eye E, an electrical line may be included to provide power from the console 24 to drive a piezoelectric device located in the handpiece 22.

This piezoelectric device helps to fragment the tissue of the lens, which can then be drawn into a port of the tip by aspiration flow. In other embodiments, the handpiece 22 is configured to remove vitreous material in the posterior chamber of the eye E, for example, by including an electrically or pneumatically driven cutter blade. In any case, a controller 30 in the console 24 is generally included to control the volume of material removed by the aspiration flow, regulate irrigation flow through handpiece 22 (or a separate probe structure), manage electrical and/or pneumatic drivers connected to the handpiece 22, and/or receive one or more input signals from sensors for monitoring the state of the system 20 during a surgical procedure.

The controller 30 may include an embedded micro-controller and/or many of the components typically found a personal computer such as a micro-processor, data bus, memory chips, input devices, and/or output drivers. The controller 30 may also include a user interface 31 and/or a foot pedal input device (not shown), and the like. Controller 30 may generally include hardware, firmware, and/or software capabilities, with the software and/or firmware typically comprising machine readable code or programming instructions for implementing one, some, or all of the methods described herein. The code may be embodied by a tangible media such as a memory, a magnetic recording media, an optical recording media, or the like. Controller 30 may have (or be coupled to) a recording media reader, or the code may be transmitted to controller 30 by a network connection such as an internet, an intranet, an Ethernet™, a wireless network, or the like. Along with programming code, controller 30 may include stored data or correlations for implementing the methods described herein, and may generate and/or store data that records parameters corresponding to the treatment of one or more patients. Many components of console 24 may be found in or modified from known commercial phacoemulsification systems from Advanced Medical Optics Inc. of Santa Ana, Calif.; Alcon Manufacturing, Ltd. of Fort Worth, Tex.; Bausch and Lomb of Rochester, N.Y.; and other suppliers.

Figure 2:
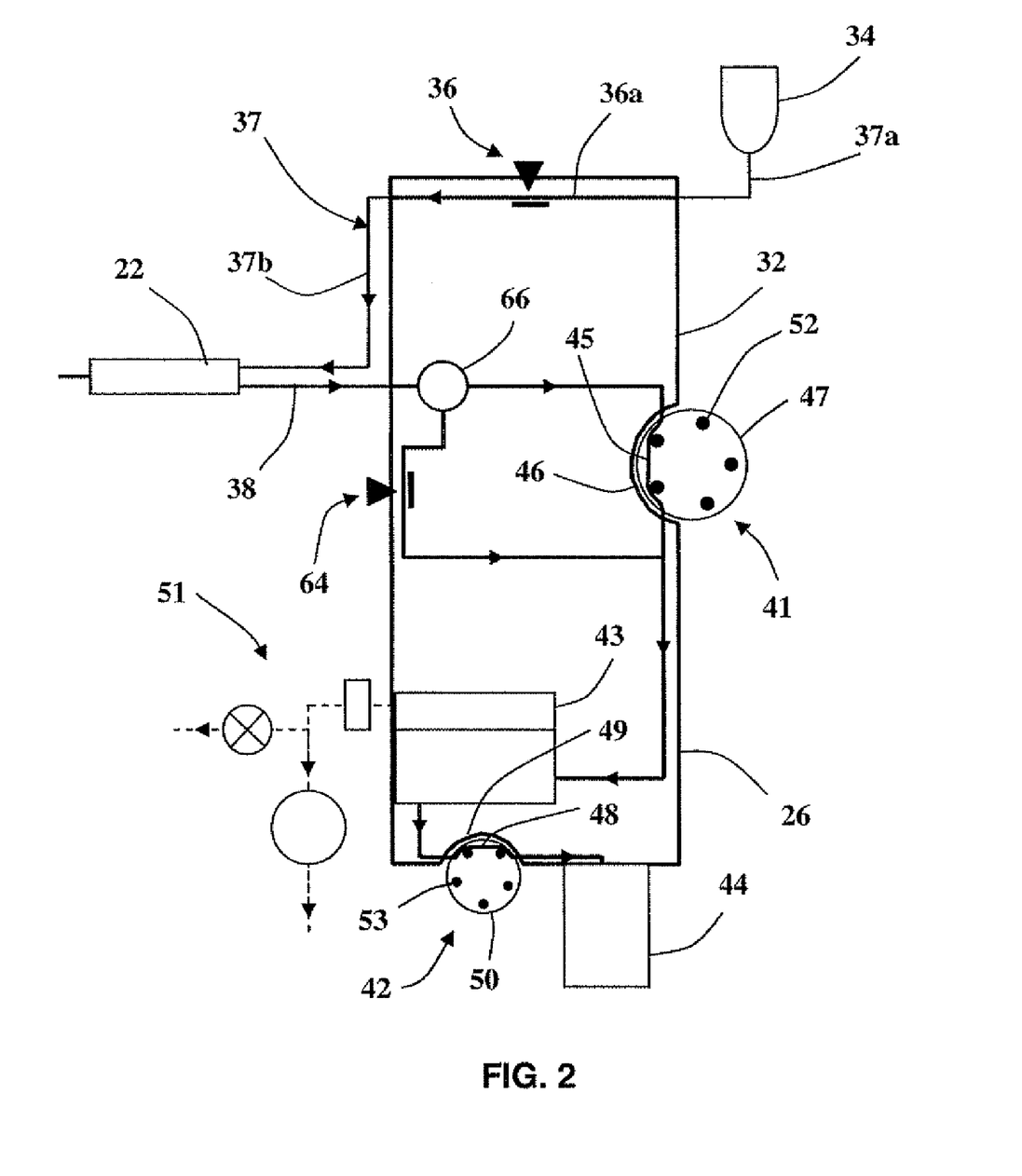
FIG. 2 is a block diagram of portions of a surgical system according to embodiments of the invention including two volumetric pumps and a vacuum system.

FIG. 2 is a schematic representation of the cassette 26 disposed within a cassette frame or housing 32 and having elements that interface with the console 24. An irrigation bottle, container, or source 34 may be used to provide irrigation fluid pressure, for example, by relying at least in part on a gravity pressure head that varies with a height of the irrigation source 34 or the like. An irrigation on/off pinch valve 36 may include a short segment of a resilient flexible conduit segment 36a within or on the cassette 26, which can be engaged and actuated by an actuator of the console 24. A surface of the cassette body 32 may be disposed opposite the actuator to facilitate closure of the conduit segment 36a. Alternative irrigation flow systems might include pumps, alternative fluid pressurization drive systems, fluid pressure or flow modulating valves, and/or the like. Regardless, the irrigation network generally defines an irrigation fluid conduit path or line 37 between irrigation source 34 and an irrigation port on the insertable probe tip of handpiece 22. The irrigation line 37 generally comprises an irrigation inlet line 37a disposed between the irrigation source 34 and the cassette 26 and an irrigation outlet line 37b disposed between the cassette 26 and the handpiece 22. The irrigation inlet and outlet lines 37a, 37b may be separate lines that attach to or inside the cassette 22. Alternatively, the irrigation inlet and outlet lines 37a, 37b may comprise a single, contiguous conduit that passes through the cassette 22. Aspiration of fluid and other matter from the eye E is provided by an aspiration line 38 that is disposed between the handpiece 22 and the cassette 26. In some embodiments, the irrigation line 37b or the aspiration line 38 may additionally or alternatively be directed to a separate handpiece (not shown) that is different from the handpiece 22.

Figure 3:
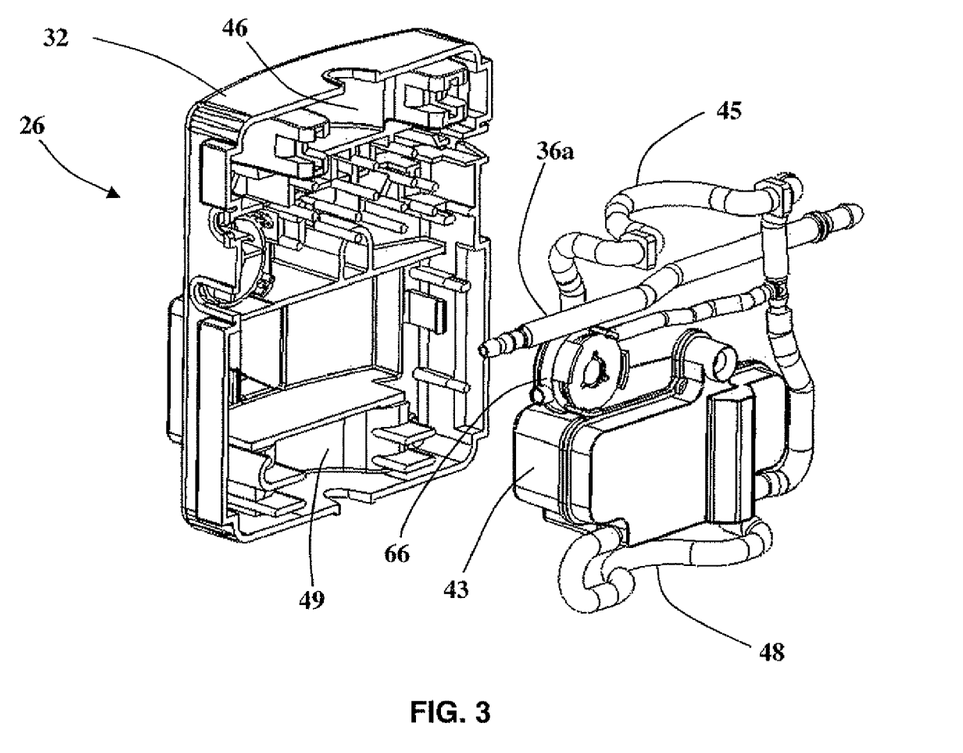
FIG. 3 is an exploded view of the cassette shown in FIG. 2.
Figure 4:
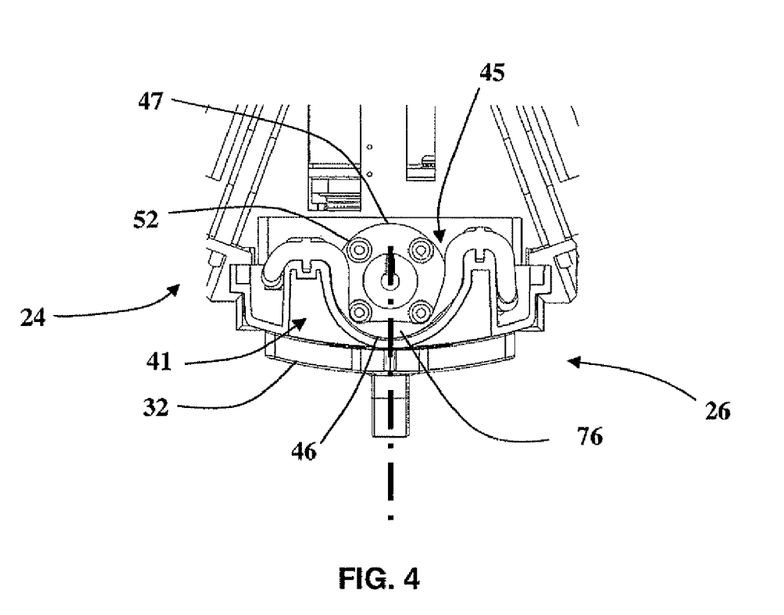
FIG. 4 is a top view of a portion of a surgical system according to embodiments of the invention illustrating the cassette shown in FIG. 3 coupled to the surgical console.

With addition additional reference to FIGS. 3 and 4, which are an exploded view of the cassette 26 and a cutaway top view of the cassette 26 and console 24, the system 20 advantageously comprises two volumetric or peristaltic pumps 41, 42 that are formed upon engagement of the cassette 26 with the console 24. The peristaltic pump 41 comprises a resilient channel 45 that is disposed between a ramp 46 in cassette 26 and a pump head 47 located in the console 24. In the illustrated embodiment, the peristaltic pump 41 is configured to provide aspiration of fluid and other material from the eye E via the handpiece 22 and the aspiration line 38. The aspiration pump 41 may be configured to rotate in one direction (counterclockwise in FIG. 2) to aspirate fluid from the eye E and into the holding tank 43 and in the opposite direction (clockwise in FIG. 2) to provide either venting or reflux operations. The drain pump 42 comprises a resilient channel 48 that is disposed between a ramp 49 in cassette 26 and a pump head 50 located in the console 24. In the illustrated embodiment, the peristaltic pump 42 is configured to control the amount of fluid in a holding tank 43 by moving material between the holding tank 43 and a waste bag 44, which may be attached to the cassette 26. The drain pump 42 is configured to transfer fluid into and/or out of the holding tank 43, depending upon the direction of rotation of the pump head 47. One or both of ramps 46, 49 may be formed integrally with the cassette body 32. Alternatively, at least one of the ramps 46, 49 may be separately fabricated and then attached to the cassette body 32. In general, the use of two peristaltic pumps in a single cassette provides for a compact design that can be fabricated in implemented into the system 20 in a relatively simple and economical fashion.

Referring to FIG. 3, various components and fluid lines disposed within the cassette body 32 are clearly visible. In particular, the resilient channels 45, 48 are seen in an uncompressed state and arcuately shaped to generally fit along the ramps 46, 49, respectively, that are formed in or on the cassette frame 32. The fluid lines in the illustrated embodiment are in the form of flexible tubing; however all or portions of the fluid lines of the cassette 26 may be replaced other types of channeling. For example, all or portions of the fluidic lines of the cassette 26 may be at least partially replaced by channels appropriately formed in a cassette frame. In some embodiments, the channels may be formed by the combination of the cassette frame 32 and a resilient cover, for example, as disclosed in U.S. Pat. No. 6,962,488.

Aspiration may additionally or alternatively be provided by a vacuum source 51 via the holding tank 43. Alternatively, the vacuum source 51 may be directly coupled directly to the aspiration line 38. Regardless, the vacuum source 51 generally comprises a Venturi pump and/or a rotary vane pump; however, other types of pumps or other vacuum sources (e.g., a vacuum line) may be used in order to produce a predetermined vacuum level in the holding tank 43. In other embodiments, other types of pumps may be used to provide aspiration capabilities to the handpiece 22, for example, a hybrid pump, such as the Concentrix pump by Bausch & Lomb, may be provided that may incorporate capabilities of both a vacuum pump and a flow pump.

The peristaltic pumps 41, 42 are generally formed by engagement of the cassette 26 with the pump heads 47, 50, respectively. The pump heads 47, 50 are usually part of the console 24; however, other configurations are possible. The pump head 47 includes one or more rotating projections, fingers, or rollers 52 disposed about an axis A1 and near a ramp 46, while pump head 50 includes one or more rotating projections, fingers, or rollers 53 disposed about an axis A2. In the illustrated embodiment, the axes A1 and A2 are collinear; however, other relationships between the axes A1 and A2 are possible (e.g., the axes may be parallel to one another, orthogonal to one another, or coplanar).

Fluid transfer by the peristaltic pump 41 is produced as the resilient channel 45 is engaged by or squeezed between the ramp 46 and one or more of the projections 52. Similarly, fluid transfer by the peristaltic pump 42 is produced as the resilient channel 48 is engaged by or squeezed between the ramp 49 and one or more of the projections 53. The resilient channels 45, 48 may be portions of a tubes made of a polymer or other suitable material. Alternatively, one or more of the resilient channels 45, 48 may be part of molded channels and/or glands that is squeezed or compressed during operation of peristaltic pumps 41, 42. Fluid aspirated through the handpiece 22 may be contained in the holding tank 43 regardless of whether the peristaltic pump 41 or the vacuum source 51 is used.

In the illustrated embodiment, the projections 52 are attached at one of their ends to a drive plate 47a and configured to rotate about an axis A1. The projections may also be commonly joined at their opposite ends to an attachment plate 47b, for example, to increase rigidity. Similarly, the projections 53 are attached at one of their ends to a drive plate 47a and configured to rotate about an axis A1. The projections may also be commonly joined at their opposite ends to an attachment plate 47b, for example, to increase rigidity.

FIG. 4, which is cutaway top view of the console 24 and the cassette 26, may be used to illustrate how the pump 41 is formed when the resilient channel 45 is engaged between the ramp 46 and the projections 52 of the pump head 47. It will be appreciated that the pump 42 is similarly formed when the resilient channel 48 is engaged the ramp 49 and the projections 53 of the pump head 50. The ramp 46 is configured to at least partially enclose at least some of the projections 52 when the cassette 26 is engaged with the console 24. As shown in FIG. 4, the resilient channel 45 is compressed between the ramp 46 and two of the projections 52. As the projections 52 rotate about the axis A1, fluid and other material entrapped within a volume 76 of the resilient channel 45 is transferred from an inlet portion of the peristaltic pump 41 to an exit portion thereof. Since the resilient channel 45 is fluidly connected to the aspiration line 38, the material is transferred from the eye E and through the peristaltic pump 41 as the resilient channel 45 is repeatedly engaged by or squeezed between the ramp 46 and the plurality of projections 52.

Referring again to FIG. 2, a selector valve 64 may be used during operation to select the source of aspiration for the handpiece 22. When the valve 64 is closed, the peristaltic pump 41 may be used for producing aspiration flow from the handpiece 22 and into the cassette 26, generally independent of the pressure in the holding tank 43. Alternatively, the vacuum source 51 may be used in conjunction with the holding tank 43 to produce aspiration flow by opening the valve 64 and halting operation of the peristaltic pump 41. When peristaltic pump 41 is not in operation, at least one of the protrusions 52 thereof pinch off the arcuate resilient channel 45, thus preventing aspiration flow therethrough. Material may rather be drawn into an aspiration port of handpiece 12 via the vacuum source 51 through the open valve 64. In this operational mode, the aspiration port draws fluid therein based on the pressure differential between holding tank 43 and the chamber of the eye E in which the fluid port is disposed. A pressure sensing device or vacuum sensor 66 may be used to determine or estimate an aspiration pressure, flow rate, line deformation, or the like, and to adjust operation of the peristaltic pump 41 and/or the vacuum source 51 so as to maintain a predetermined flow rate or pressure level at the vacuum sensor 66 or elsewhere within the system. In some embodiments, the vacuum sensor 66 is coupled to the console 24 to provide a pressure sensing mechanism providing an output that is used by the controller 30 to control one or more aspects of the system 20.

Figure 5:
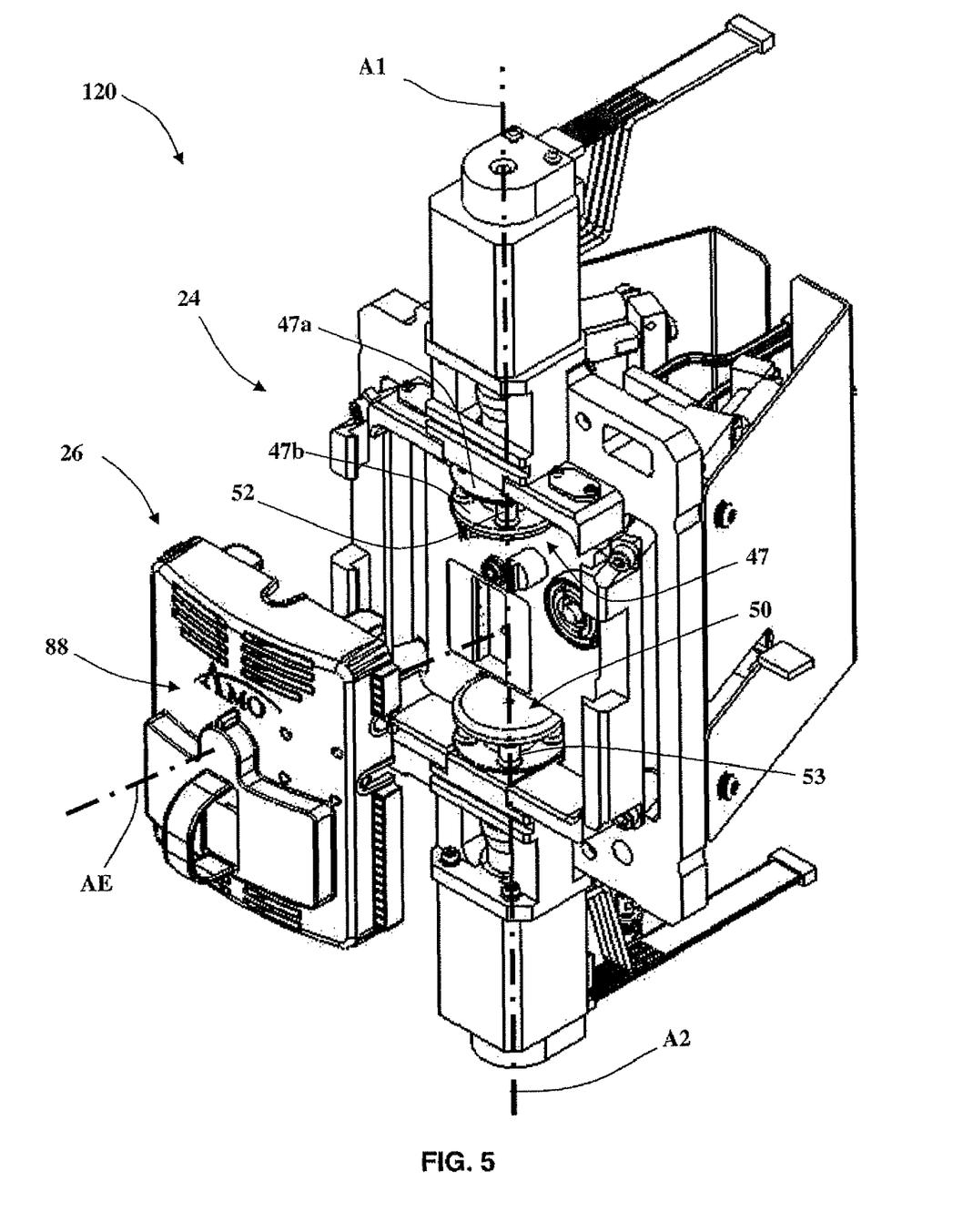
FIG. 5 is a perspective view of the surgical system illustrated in FIG. 2 showing the fluidics cassette in FIG. 3 separated from the surgical console.
Figure 6:
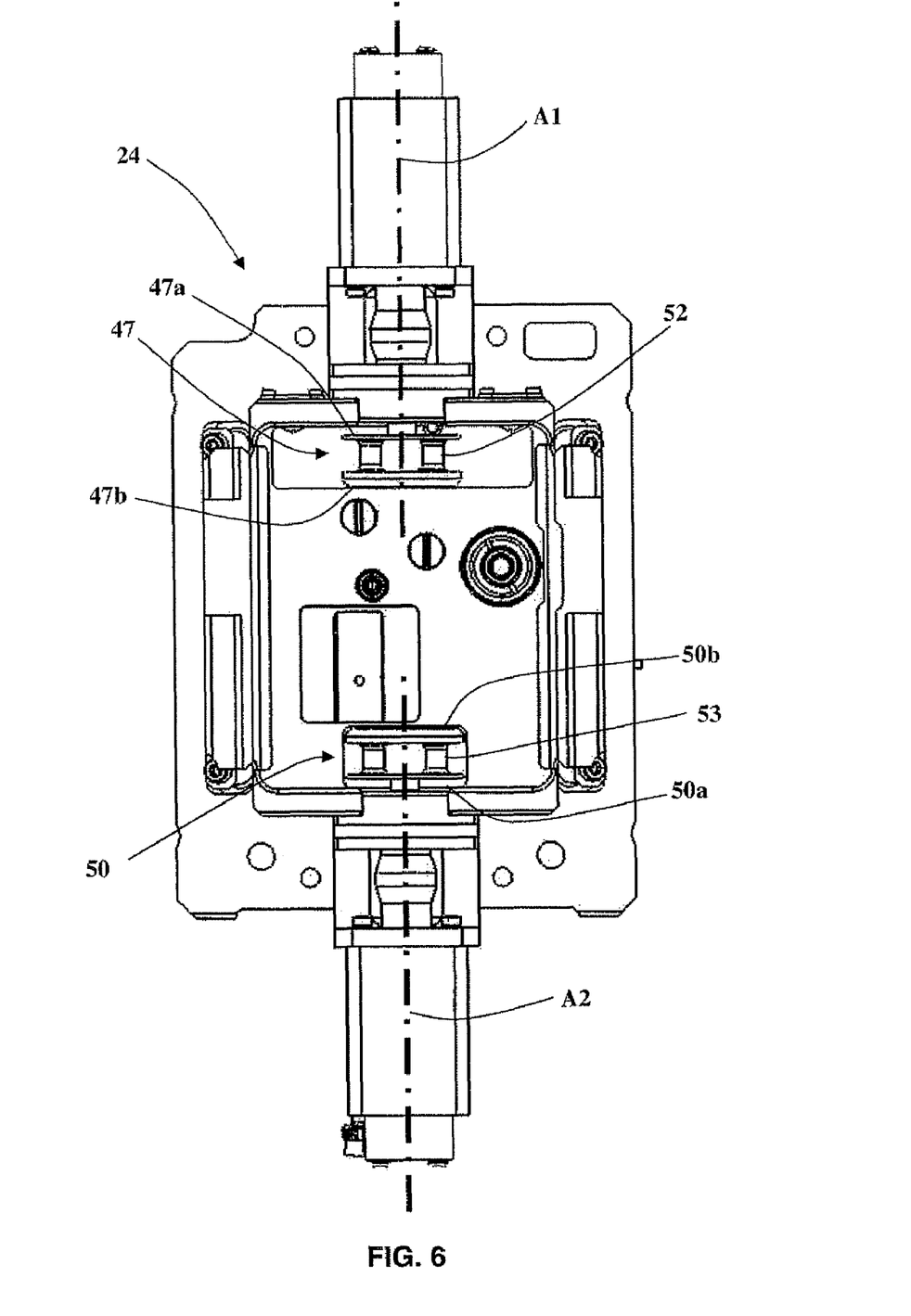
FIG. 6 is a front view of the surgical console shown in FIG. 5.
Figure 7:
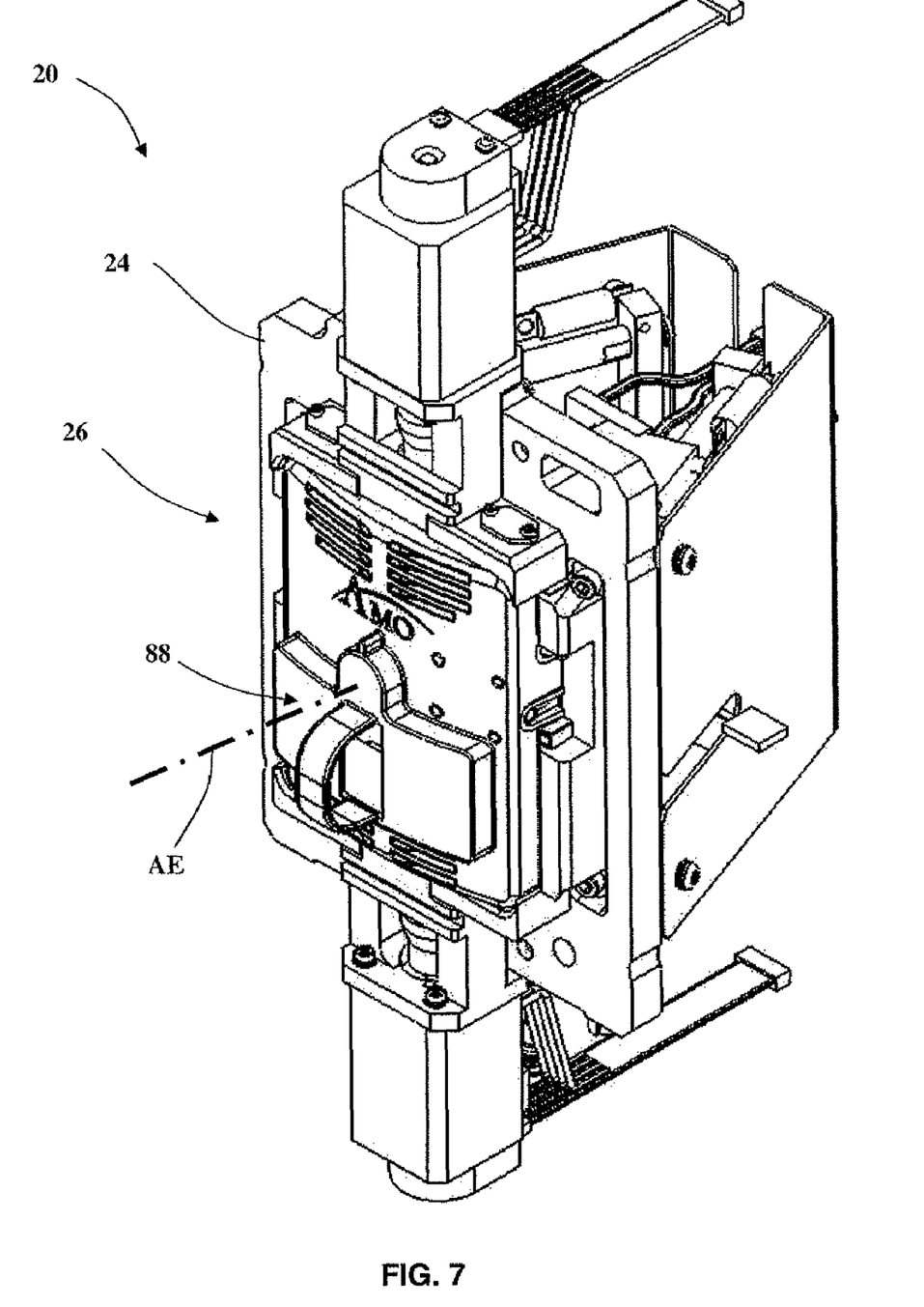
FIG. 7 is a perspective view of the surgical system illustrated in FIG. 5 showing the cassette coupled to the surgical console.

FIGS. 5-7 illustrate perspective and front views of a portion of the system 20 that is schematically illustrated in FIG. 2, illustrating various elements of the console 22 and the cassette 26. For clarity, the handpiece 22 and the irrigation source 34 are not illustrated in the FIGS. 5-7, Referring to FIG. 5, the cassette 26 is shown separated from the console 24, while in FIG. 7 the cassette 26 is shown engaged with the console 24 so as to couple a handpiece or eye treatment probe with the console 24. The system comprises engagement axis AE along which elements of the cassette 26 are configured to generally engage with mating elements of a console 24.

Figure 8:
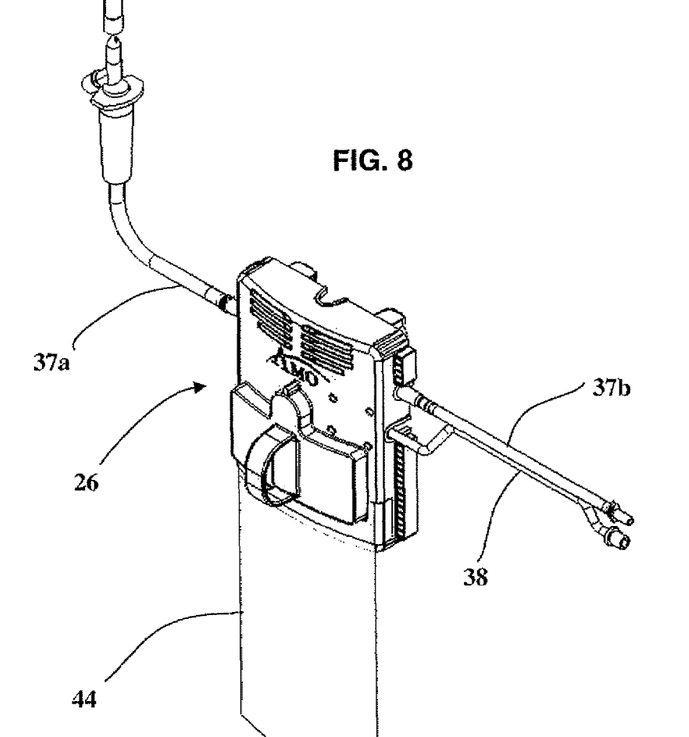
FIG. 8 is a front perspective view of the cassette shown in FIG. 3.
Figure 9:
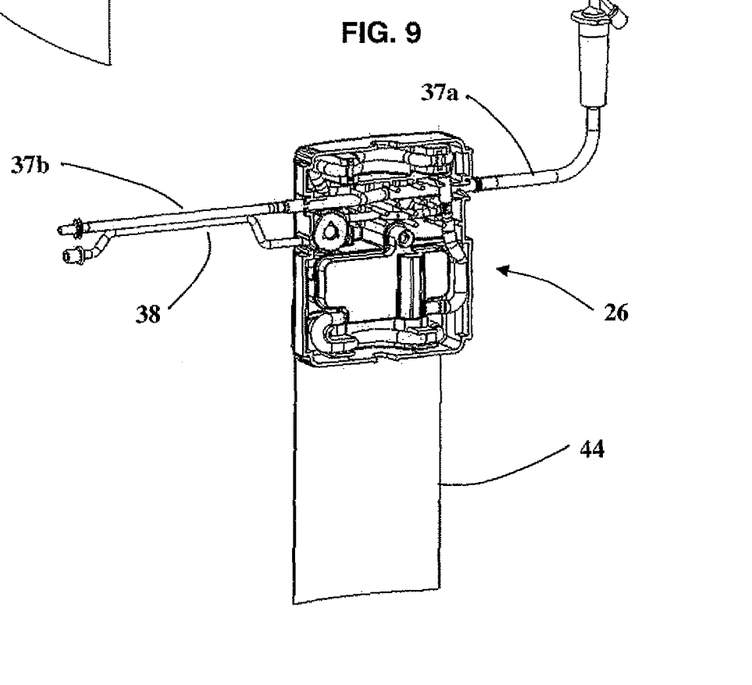
FIG. 9 is a rear perspective view of the cassette shown in FIG. 3.

FIGS. 8 and 9 illustrate the cassette 26 with associated components of the system 20, including but not limited to, irrigation inlet and outlet lines 37a, 37b, aspiration line 38, waste bag 44, holding tank 43, and vacuum sensor 66. The irrigation and aspiration lines 37b, 38 are configured to be coupled to the handpiece 22, allowing the cassette 26 to provide at least irrigation fluid to, and aspiration of fluid from, the eye E.

Figure 10:
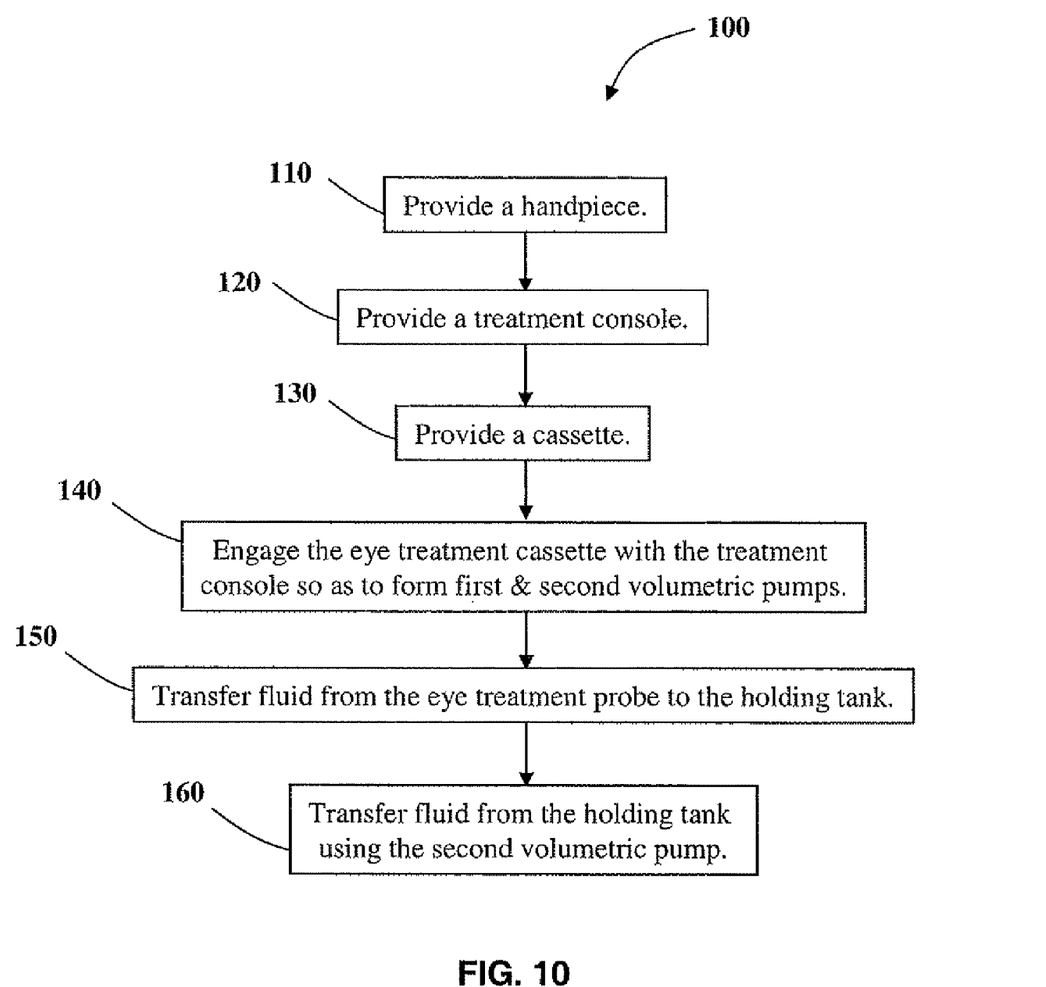
FIG. 10 is a block diagram of a method according to an embodiment of the present invention.

Referring to FIG. 10, in certain embodiments, a method 100 of using an eye treatment system 20 comprises an operational block 110 of providing a handpiece configured to provide irrigation and aspiration functions. The method 100 also comprises an operational block 120 of providing a treatment console according to embodiments of the invention. The method 100 additionally comprises an operational block 130 of providing a cassette according to embodiments of the invention that includes a holding tank. The method 100 further comprises an operational block 140 of engaging the eye treatment cassette with the treatment console so as to form a first volumetric pump and a second volumetric pump. The method 100 additionally comprises an operational block 150 of transferring fluid from the eye treatment probe to the holding tank using the first volumetric pump or vacuum pump. The method 100 also comprises an operational block 160 of transferring fluid from the holding tank using the second volumetric pump.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. An eye treatment cassette for use in an eye treatment system for coupling an eye treatment probe with a treatment console, the cassette comprising:
   a cassette body;
   irrigation and aspiration lines configured to provided irrigation and aspiration functions to an eye treatment probe;

a first arcuate ramp provided within the cassette body and proximal a first fluidics channel configured to form a first volumetric pump after engagement of the first fluidics channel with the first arcuate ramp and a first rotating element associated with a treatment console;

a second arcuate ramp provided within the cassette body and proximal a second fluidics channel configured to form a second volumetric pump upon engagement of the second fluidics channel with the second arcuate ramp and a second rotating element associated with the treatment console; and a holding tank configured to be fluidly coupled to the volumetric pumps.

2. The eye treatment cassette of claim 1, wherein at least one of the first and second arcuate ramps is configured to form a peristaltic pump upon engagement with the treatment console.

3. The eye treatment cassette of claim 1, further comprising an engagement axis along which elements of the cassette are configured to generally engage with mating elements of a treatment console, wherein the first arcuate ramp is disposed about a first axis lying within a plane orthogonal to the engagement axis and the second arcuate ramp is disposed about a second axis lying within a plane orthogonal to the engagement.

4. The eye treatment cassette of claim 3, wherein the first axis and the second axis are coplanar.

5. The eye treatment cassette of claim 3, wherein the first axis and the second axis are collinear.

6. The eye treatment cassette of claim 1, wherein the first fluidics channel is fluidly coupled to the holding tank and the eye treatment probe, the second fluidics channel is fluidly coupled to the holding tank.

7. The eye treatment cassette of claim 1, wherein the holding tank comprises a vacuum coupler configured to connect the holding tank to a vacuum source.

8. The eye treatment cassette of claim 7, wherein the vacuum source is a Venturi pump.

9. An eye treatment system for performing an ocular surgical procedure, comprising:
    an eye treatment probe configured to provide at least irrigation fluid to, and aspiration of fluid from, a subject eye;
    a treatment console having a controller;
    an eye treatment cassette for coupling the eye treatment probe with the treatment console, the cassette comprising:
    a cassette body;
    an engagement axis along which elements of the cassette are configured to generally engage with mating elements of the treatment console;
    a first arcuate ramp provided within the cassette body and proximal a first fluidics channel configured to form a first volumetric pump upon engagement of the first fluidics channel with the first arcuate ramp and a first rotating element associated with the treatment console;
    a second arcuate ramp provided within the cassette body and proximal a second fluidics channel configured to form a second volumetric pump upon engagement of the second fluidics channel with the second arcuate ramp and a second rotating element associated with the with the treatment console; and
    a holding tank fluidly coupled to the volumetric pumps.

10. The eye treatment system of claim 9, wherein the first arcuate ramp is disposed about a first axis lying within a plane orthogonal to the engagement axis and the second arcuate ramp is disposed about a second axis lying within a plane orthogonal to the engagement.

11. The eye treatment system of claim 9, wherein the eye treatment probe further comprises an ultrasonic driver configured to emulsify a lens of the eye.

12. The eye treatment system of claim 9, wherein the first fluidics channel is in fluid communication with the holding tank and the eye treatment probe, the second fluidics channel is in fluid communication with the holding tank.

13. The eye treatment system of claim 9, wherein the treatment console comprises a vacuum pump and the holding tank comprises a vacuum coupler configured to couple the holding tank with the vacuum pump.

14. An eye treatment system for performing an ocular surgical procedure, comprising:
    an eye treatment probe configured to provide at least irrigation fluid to, and aspiration of fluid from, a subject eye;
    a treatment console having a controller;
    an eye treatment cassette comprising a fluid holding tank, the cassette engaging the treatment console so as to couple the eye treatment probe with the treatment console;
    first and second peristaltic pumps formed by the engagement of the cassette with first and second rotating elements, respectively, associated with the treatment console;
    the first peristaltic pump configured to transfer fluid from the eye treatment probe to the fluid holding tank; and
    the second peristaltic pump configured to transfer fluid from the fluid holding tank.

15. A method of using an eye treatment system, comprising:
    providing an eye treatment probe configured to provide at least irrigation fluid to, and aspiration of fluid from, a subject eye;
    providing a treatment console having a controller;
    providing an eye treatment cassette having a fluid holding tank;
    engaging the eye treatment cassette with first and second rotating elements associated with the treatment console so as to form a first peristaltic pump and a second peristaltic pump;
    transferring fluid from the eye treatment probe to the fluid holding tank using the first peristaltic pump;
    transferring fluid from the fluid holding tank using the second peristaltic pump.

16. The method of claim 15, further comprising providing an ultrasonic driver configured to emulsify a lens of the eye and configuring the controller to control the ultrasonic driver.

17. A treatment cassette for use in a surgical or other medical procedure, the cassette comprising:
    a cassette body;
    an engagement axis along which elements of the cassette are configured to generally engage with mating elements of a console;
    a first arcuate ramp provided within the cassette body and configured to engage a first fluidics channel to form a first volumetric pump upon engagement between the first fluidics channel, the first arcuate ramp, and a first rotating element associated with the console, the first arcuate ramp disposed about a first axis lying within a plane orthogonal to the engagement axis; and
    a second arcuate ramp provided within the cassette body and configured to engage a second fluidics channel to form a second volumetric pump upon engagement between the second fluidics channel, the second arcuate ramp, and a second rotating element associated with the console, the second arcuate ramp disposed about a second axis lying within a plane orthogonal to the engagement axis.

18. The eye treatment system of claim 1, wherein the holding tank is housed within the cassette body.

19. The eye treatment system of claim 9, wherein the holding tank is housed within the cassette body.

20. The eye treatment system of claim 14, wherein the holding tank is housed within the cassette body.

21. The eye treatment system of claim 15, wherein the holding tank is housed within the cassette body.

* * * * *